United States Patent [19]

Sheu et al.

[11] Patent Number: 5,436,376
[45] Date of Patent: Jul. 25, 1995

[54] PRODUCTION OF TERTIARY BUTYL ALCOHOL

[75] Inventors: Yu-Hwa E. Sheu, Hsinchu, Taiwan; John R. Sanderson, Leander, Tex.; Mark A. Mueller, Austin, Tex.; William A. Smith, Houston, Tex.

[73] Assignee: Texaco Chemical Inc., White Plains, N.Y.

[21] Appl. No.: 288,841

[22] Filed: Aug. 11, 1994

[51] Int. Cl.$^6$ .................. C07C 29/48; C07C 29/80; C07C 31/12; C07C 29/88
[52] U.S. Cl. .................. 568/910; 549/529; 568/698; 568/909.8; 568/922
[58] Field of Search .................. 568/909.8, 910, 922

[56] References Cited

U.S. PATENT DOCUMENTS

| | | | |
|---|---|---|---|
| 2,845,461 | 7/1958 | Winkler et al. | 568/910 |
| 4,547,598 | 10/1985 | Sanderson et al. | 568/922 |
| 4,704,482 | 11/1987 | Sanderson et al. | 568/922 |
| 4,705,903 | 11/1987 | Sanderson et al. | 568/922 |
| 4,742,179 | 5/1988 | Sanderson et al. | 568/913 |
| 4,873,380 | 10/1989 | Sanderson et al. | 568/914 |
| 4,912,267 | 3/1990 | Sanderson et al. | 568/909.8 |
| 5,093,506 | 3/1992 | Marquis et al. | 568/909.8 |
| 5,236,893 | 8/1993 | Sanderson et al. | 568/909.8 |
| 5,354,917 | 10/1994 | Sanderson et al. | 568/909.8 |

FOREIGN PATENT DOCUMENTS 3248465 7/1984 Germany .................. 568/910
260528 12/1985 Japan .................. 568/909.8

Primary Examiner—Joseph E. Evans
Attorney, Agent, or Firm—James L. Bailey; Kenneth R. Priem; Carl G. Ries

[57] ABSTRACT

A plural stage process for the production of tertiary butyl alcohol from isobutane wherein isobutane is reacted with oxygen in a first reactor to prepare a primary liquid reaction mixture comprising unreacted isobutane, tertiary butyl alcohol, tertiary butyl hydroperoxide and small amounts of oxygen-containing by-products, distilling the primary reaction product to provide a first lighter isobutane recycle distillation fraction and a first heavier liquid distillation fraction comprising the debutanized mixture of tertiary butyl hydroperoxide with tertiary butyl alcohol, diluting the first heavier liquid distillation fraction with an amount of tertiary butyl alcohol sufficient to provide a feed mixture comprising about 15 to 25 wt. % of tertiary butyl hydroperoxide, about 75 to 85 wt. % of tertiary butyl alcohol and minor amounts of oxygen-containing impurities, wherein the feed mixture is charged to a hydroperoxide decomposition reactor and contacted therein with a solid heterogeneous hydroperoxide decomposition catalyst to convert substantially all of the tertiary butyl hydroperoxide to tertiary butyl alcohol and a minor amount of oxygen-containing by-products to provide a final reaction mixture and wherein tertiary butyl alcohol is recovered from the final reaction mixture.

1 Claim, 1 Drawing Sheet

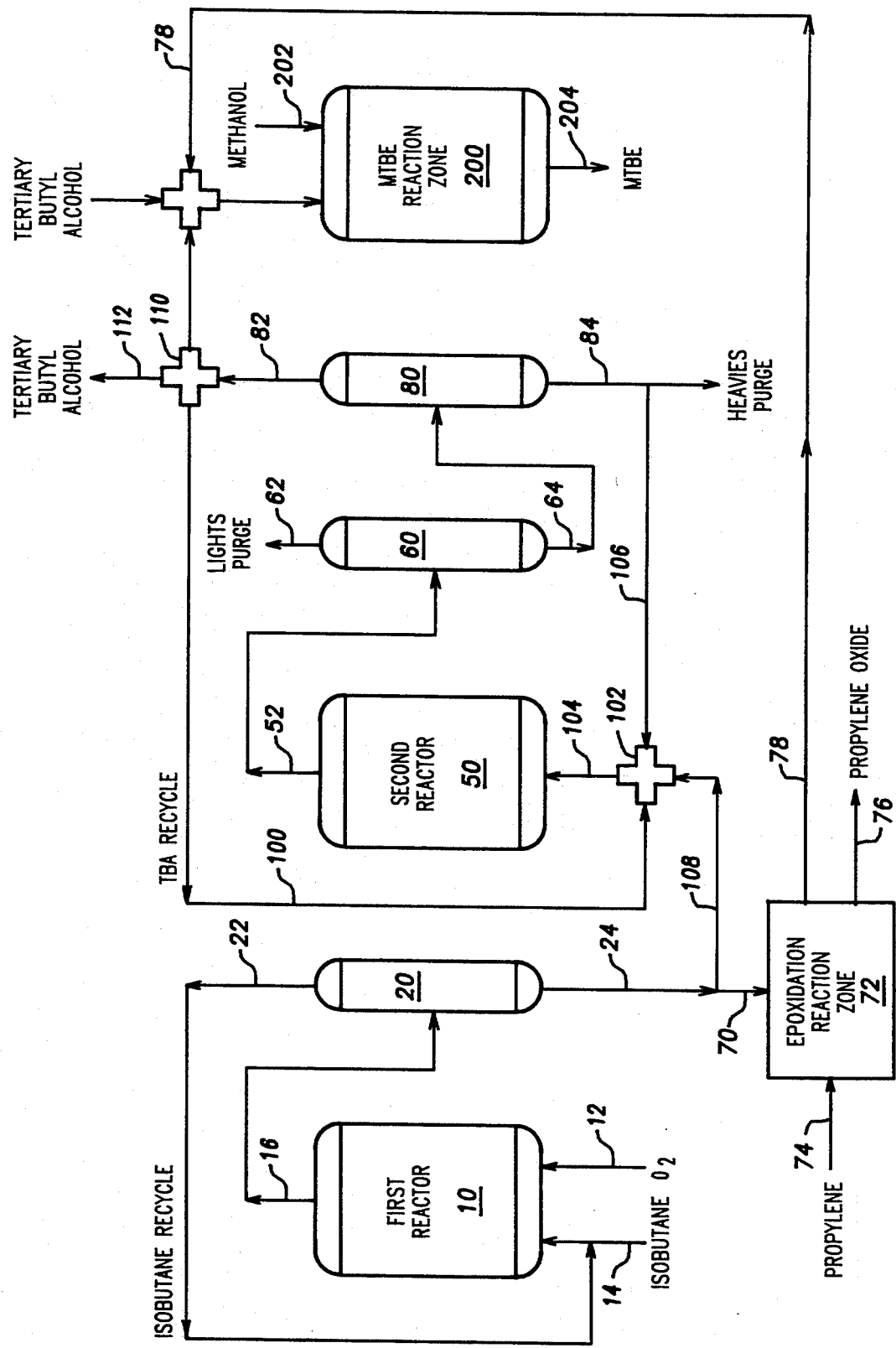

5,436,376

PRODUCTION OF TERTIARY BUTYL ALCOHOL

BACKGROUND OF THE INVENTION

1. Field of the Invention

This invention relates to a plural stage process for the production of tertiary butyl alcohol from isobutane. More particularly, this invention relates to a plural stage process for the production of tertiary butyl alcohol from isobutane wherein isobutane is first non-catalytically reacted with oxygen in an oxidation reactor to prepare a primary liquid reaction product comprising unreacted isobutane, tertiary butyl alcohol, tertiary butyl hydroperoxide and small amounts of oxygen-containing by-products such as ditertiary butyl peroxide, methanol, acetone, methyl formate, water, etc., wherein the primary liquid reaction product is fractionated so as to provide a first lighter isobutane recycle distillation fraction and a first heavier liquid distillation fraction comprising the remainder of the primary liquid reaction mixture, wherein the second heavier liquid distillation fraction is diluted with an amount of tertiary butyl alcohol sufficient to provide a charge mixture comprising about 15 to 20 wt. % of tertiary butyl hydroperoxide, about 80 to 85 wt. % of tertiary butyl alcohol and minor amounts of oxygen-containing impurities, wherein the charge mixture is brought into contact with a solid heterogeneous peroxide decomposition catalyst in a hydroperoxide decomposition reactor to convert substantially all of the tertiary butyl hydroperoxide to tertiary butyl alcohol, a minor portion being converted to oxygen-containing by-products and wherein tertiary butyl alcohol is recovered.

2 Prior Art

It is known to non-catalytically react isobutane with oxygen in the liquid phase in order to provide a reaction product comprising a mixture of tertiary butyl hydroperoxide with tertiary butyl alcohol as illustrated, for example, by Winkler et al. U.S. Pat. No. 2,845,461.

It is known to react isobutane with oxygen in the presence of a peroxidation catalyst in order to provide a reaction product comprising tertiary butyl alcohol and residual tertiary butyl hydroperoxide as shown, for example, by Grane et al. U.S. Pat. No. 4,294,999, Grane et al. U.S. Pat. No. 4,296,262 and Worrell U.S. Pat. No. 4,296,263.

It is known to prepare tertiary butyl alcohol by the catalyzed decomposition of tertiary butyl hydroperoxide as shown, for example, by Sanderson et al. U.S. Pat. No. 4,547,598.

It is known to purify tertiary butyl alcohol by the catalytic decomposition of residual quantities of tertiary butyl hydroperoxide contained therein using a catalyst, as shown, for example, by Sanderson et al. U.S. Pat. No. 4,705,903, Sanderson et al. U.S. Pat. No. 5,159,122, and Sanderson et al. U.S. Pat. No. 5,185,480.

It is known to use tertiary butyl hydroperoxide prepared by the oxidation of isobutane, as a feedstock, together with propylene for an epoxidation reaction process wherein the propylene and tertiary butyl hydroperoxide are converted to propylene oxide and tertiary butyl alcohol as shown, for example, by Marquis et al. U.S. Pat. No. 5,093,506 and Marquis et al. U.S. Pat. No. 5,151,530.

It is known to use tertiary butyl alcohol obtained by the oxidation of isobutane as a feedstock, together with methanol as a feedstock, for an etherification reaction process wherein the tertiary butyl alcohol and methanol are reacted to form methyl tertiary butyl ether. See, for example, Kruse et al. U.S. Pat. No. 5,243,091.

SUMMARY OF THE INVENTION

In accordance with the present invention, tertiary butyl alcohol is prepared from isobutane by non-catalytically reacting isobutane with oxygen in an oxidation reactor to provide a primary liquid reaction mixture comprising isobutane, peroxides including tertiary butyl hydroperoxide, and ditertiary butyl peroxide and oxygen-containing impurities including methanol, methyl formate, acetone and water. The primary liquid reaction mixture will typically comprise about 15 to about 25 wt. % of tertiary butyl hydroperoxide, about 13 to about 20 wt. % of tertiary butyl alcohol, about 50 to about 65 wt. % of unreacted isobutane and about 2 to about 5 wt. % of oxygen-containing impurities.

The primary reaction mixture is separated in any suitable manner (e.g., by distillation) so as to provide a first lighter isobutane recycle distillation fraction and a first heavier liquid distillation fraction substantially free from isobutane comprising about 40 to about 55 wt. % of tertiary butyl hydroperoxide, about 45 to 50 wt. % of tertiary butyl alcohol and about 3 to about 5 wt. % of oxygen-containing impurities. A portion of the first heavier liquid distillation fraction, which is composed of a mixture of tertiary butyl hydroperoxide with tertiary butyl alcohol may be used together with propylene, as the charge stock for a plant to manufacture propylene oxide and tertiary butyl alcohol from tertiary butyl hydroperoxide and propylene.

In accordance with the present invention, all or a part of the first heavier liquid distillation fraction comprising the debutanized mixture of tertiary butyl hydroperoxide with tertiary butyl alcohol is diluted with an Mount of tertiary butyl alcohol sufficient to provide a charge mixture comprising about 15 to 25 wt. % of tertiary butyl hydroperoxide, about 75 to 85 wt. % of tertiary butyl alcohol and about 2 to about 5 wt. % of oxygen-containing impurities. In accordance with the present invention, the charge mixture is brought into contact with a solid heterogeneous peroxide decomposition catalyst in a hydroperoxide decomposition reactor to convert substantially all of the tertiary butyl hydroperoxide to tertiary butyl alcohol and a minor amount of oxygen-containing by-products and to provide a final reaction product. Tertiary butyl alcohol may be recovered from the final reaction product in any suitable manner, such as by distillation.

DESCRIPTION OF THE PROCESS OF THE PRESENT INVENTION

Feedstocks

The feedstocks to be used in accordance with the present invention are isobutane and oxygen. The isobutane may be used in purified form or as a component of a butane fraction containing other butanes such as normal butane. The oxygen may be used as concentrated molecular oxygen or as air, in which case nitrogen will be present as a diluent.

THE NON-CATALYTIC OXIDATION OF ISOBUTANE

In accordance with the present invention, the initial reaction of isobutane with oxygen is conducted on a non-catalytic basis for a number of reasons. An enhanced amount of tertiary butyl hydroperoxide is formed which can be used in the manufacture of propylene oxide whereas when a catalyst is used the production of tertiary butyl hydroperoxide is limited. Also, if a catalyst is present, the tertiary butyl hydroperoxide will be contaminated with a trace quantity of soluble metals which are deleterious in a propylene oxidation process.

The initial reaction of isobutane with oxygen is conducted in accordance with the present invention in the manner known to those skilled in the art, as exemplified for example, by Winkler et al. U.S. Pat. No. 2,845,461. Thus, liquid isobutane is charged to an oxidation reactor together with oxygen and oxidation reaction conditions are established therein including, for example, a temperature of about 90° to about 150° C. and a pressure of about 50 to about 1000 psig in order to non-catalytically convert a portion of the isobutane to oxidation products including tertiary butyl alcohol, tertiary butyl hydroperoxide and minor amounts of oxygen-containing by-products including ditertiary butyl peroxide, methanol, methyl formate, acetone and water. The thus-formed primary liquid reaction mixture will typically comprise about 15 to about 25 wt. % of tertiary butyl hydroperoxide, about 13 to about 20 wt. % of tertiary butyl alcohol, about 50 to about 65 wt. % of unreacted isobutane and about 2 to about 5 wt. % of oxygen-containing impurities.

The primary liquid reaction product is separated in any suitable manner (e.g., by distillation) so as to provide a first lighter isobutane recycle distillation fraction and a first heavier liquid distillation fraction substantially free from isobutane comprising about 40 to about 55 wt. % of tertiary butyl hydroperoxide, about 45 to 50 wt. % of tertiary butyl alcohol and about 3 to about 5 wt. % of oxygen-containing impurities.

THE CATALYTIC HYDROPEROXIDE DECOMPOSITION STEP

In accordance with the present invention, all or a part of the first heavier liquid distillation fraction comprising the debutanized mixture of tertiary butyl hydroperoxide with tertiary butyl alcohol is diluted with an amount of tertiary butyl alcohol sufficient to provide a charge mixture comprising about 15 to 25 wt. % of tertiary butyl hydroperoxide, about 75 to 85 wt. % of tertiary butyl alcohol and about 2 to about 5 wt. % of oxygen-containing impurities. In accordance with the present invention, the charge mixture is brought into contact with a solid heterogeneous peroxide decomposition catalyst in a reactor to convert substantially all of the tertiary butyl hydroperoxide to tertiary butyl alcohol, and a minor amount of oxygen-containing by-products and to provide a final reaction product.

Thus, the charge mixture that is charged to the hydroperoxide decomposition reactor is brought into contact with a bed of a solid heterogeneous hydroperoxide decomposition catalyst under reaction conditions including a temperature of about 25° to 250° C., a pressure of about 20 to about 1,000 psig, and a reaction time of about 0.1 to about 10 hours, and more preferably a reaction temperature of about 60° to 120° C., a reaction pressure of about 50 to 500 psig, and a reaction time of about 0.5 to 5 hours.

The liquid reaction product formed in the hydroperoxide decomposition reactor will comprise tertiary butyl alcohol, but will contain a minor amount (e.g., about 10 to 1000 ppm) of unreacted tertiary butyl hydroperoxide and other peroxide contaminants as well as heavier reaction byproducts such as carboxylic acids.

It is known to prepare tertiary butyl alcohol by the catalytic decomposition of tertiary butyl hydroperoxide. Thus, Sanderson et al. U.S. Pat. No. 4,547,598 discloses the use of heterogeneous cobalt borate catalysts such as titania-supported cobalt borate catalysts for the decomposition of hydroperoxides such as tertiary butyl hydroperoxide. Sanderson et al. U.S. Pat. No. 4,705,903 discloses that heterogeneous catalysts composed of iron, copper, chromia and cobalt can be used for the decomposition of hydroperoxides such as tertiary butyl hydroperoxide. In Sanderson et al. U.S. Pat. No. 5,159,122 acid treated clay is used for the decomposition of hydroperoxides. Sanderson et al. U.S. Pat. No. 5,185,480 discloses that heterogeneous catalysts composed of transition metals such as iron, copper, nickel, cobalt, chromium, aluminum, iron, calcium magnesium and manganese can be used for the decomposition of hydroperoxides such as tertiary butyl hydroperoxide.

A preferred catalyst is Pd/Av on $Al_2O_3$.

In a continuous process, the space velocity is suitably within the range of about 0.5 to 5 volumes of tertiary butyl hydroperoxide charge stock per volume of pelleted catalyst per hour.

When the process of the present invention is practiced in a continuous manner by continuously charging the feed mixture to a hydroperoxide decomposition reactor containing a fixed bed of pelleted hydroperoxide decomposition catalyst, the space velocity is suitably in the range of about 0.5 to about 5 volumes of tertiary butyl hydroperoxide charge stock per volume of catalyst per hour. Preferably, the space velocity is within the range of about 0.5 to about 2 volumes of tertiary butyl hydroperoxide charge stock per volume of catalyst per hour.

The final liquid reaction product which will comprise tertiary butyl alcohol, from about 10 to about 1000 ppm of peroxide impurities, and from about 3 to about 5 wt. % of oxygen-containing impurities including methanol, acetone and water, as well as normally gaseous by-products such as oxygen, is withdrawn from the hydroperoxide decomposition reactor and charged to a second distillation column wherein it is separated into a third light overhead fraction comprising oxygen, and vaporized normally liquid components including tertiary butyl alcohol, water and oxygenated impurities including acetone and methanol.

A heavier distillation fraction is withdrawn from the second distillation column comprising tertiary butyl alcohol, residual peroxide contaminants, solubilized catalysts, and heavier byproducts such as carboxylic acids. The heavier liquid fraction is recycled to the hydroperoxide decomposition reactor in accordance with the preferred embodiment of the present invention.

As indicated previously, all or a portion of the tertiary butyl alcohol reaction products may be used as feedstocks for the manufacture of methyl tertiary butyl ether. When this is to be done, the tertiary butyl alcohol from the hydroperoxide decomposition reactor is charged, together with methanol, to an appropriate methyl tertiary butyl preparation unit where they are reacted in the presence of an appropriate catalyst to provide methyl tertiary butyl ether. A representative process of this nature is disclosed, for example, in Kruse et al. U. S. Pat. No. 5,243,091.

As indicated, a portion of the first heavier liquid distillation fraction comprising debutanized initial reaction product may be utilized as a feedstock for the preparation of propylene oxide and additional tertiary butyl alcohol. When this is to be done, a portion of the first heavier liquid distillation fraction and propylene are charged to an epoxidation reaction unit where they are catalytically reacted in the presence of a soluble molybdenum catalyst to provide propylene oxide and additional tertiary butyl alcohol. A representative process of this nature is disclosed, for example, in Marquis et al. U.S. Pat. No. 5,093,506 and No. 5,151,530.

BRIEF DESCRIPTION OF THE DRAWINGS

In the drawings:
the FIGURE is a schematic flow sheet illustrating a preferred method for the practice of the present invention.

Turning now to the drawing, there is schematically shown an oxidation reactor 10 to which oxygen is charged by a line 12 and to which isobutane is charged by a line 14.

Non-catalytic oxidation reaction conditions are established in the oxidation reactor 10 correlated to provide a primary liquid reaction mixture comprising unreacted butane, peroxide reaction products including tertiary butyl hydroperoxide, ditertiary butyl peroxide, etc., tertiary butyl alcohol, oxygenated impurities including methanol and acetone, water and oxygen. Suitably, the non-catalytic reaction conditions used in the first reactor 10 will include a temperature of about 90° to about 150° C., a pressure of about 50 to about 1000 psig, and a reaction time of about 1 to about 8 hours. A primary liquid reaction mixture having the described composition is continuously withdrawn from the reactor 10 by way of a discharge line 16 leading to a first distillation column 20 wherein the primary reaction mixture is fractionated under conditions selected to provide for an overhead light distillation fraction 22 consisting essentially of isobutane and a bottoms heavier distillation fraction comprising the remainder of the primary liquid reaction product which is discharged by way of a line 24. All or a portion of the isobutane in the line 22 may be recycled to the isobutane charge line 14 for the first reactor 10.

The hydroperoxide decomposition reactor 50 will contain a fixed bed of peroxide decomposition catalyst such as a noble metal decomposition catalyst (e.g., platinum or palladium deposited on silica). The charge mixture 104 will be charged to peroxide decomposition reactor 50 under reaction conditions of time, temperature and pressure therein sufficient to substantially decompose the peroxides in the feed mixture and to form a final reaction product comprising tertiary butyl alcohol, minor quantities of peroxide impurities, oxygen-containing impurities including methanol, acetone and water, and minor quantities of oxygen. Suitably, the reaction conditions within the hydroperoxide decomposition reactor 50 will comprise a temperature of about 25° to about 250° C., and more preferably from about 60° to about 120° C., a pressure of about 20 to about 1000 psig and more preferably from about 50 to about 500 psig, and a reaction time of about 0.1 to about 10 hours and more preferably from about 0.5 to about 5 hours. The final reaction product is discharged from the reactor 50 by a line 52 leading to a second distillation column 60 wherein it is separated into a lighter overhead distillation fraction 62 comprising oxygen and vaporized normally liquid components including tertiary butyl alcohol, water and oxygenated impurities including acetone and methanol, and a heavier fraction 64 comprising normally liquid products including tertiary butyl alcohol, and residual quantities of peroxide contaminants.

The fraction 64 is charged to a third distillation column 80 where it is separated into a purified overhead tertiary butyl alcohol distillation product fraction 82 and a bottoms distillation fraction 84 comprising heavier reaction by-products and contaminants.

The tertiary butyl alcohol is charged by the line 82 to a manifold 110. A portion of the tertiary butyl alcohol may be recovered as product, if desired, by a line 112. A portion of the tertiary butyl alcohol is recycled by a line 100 as diluent to a manifold 102 leading to a charge line 104 for the peroxide decomposition reactor 50. The heavier liquid distillation fraction 24 is also charged to the manifold 102 by a charge line 108. A portion of the bottoms fraction 84 from the third distillation column 80 may also be recycled by way of branch line 106 to manifold 102 and then to the second reactor 50.

In accordance with one embodiment of the present invention, a portion of the heavier liquid distillation fraction 24 is charged by way of a line 70 to an epoxidation reaction zone 72. Propylene is also charged to the epoxidation reaction zone 72 by a line 74. Within the epoxidation reaction zone 72 propylene and tertiary butyl hydroperoxide contained in the first heavier liquid distillation fraction 70 react in the presence of a soluble molybdenum catalyst to form propylene oxide and additional tertiary butyl alcohol. The epoxidation reaction zone may be constructed and operated in the manner disclosed and described in Marquis et al. U.S. Pat. No. 5,151,530.

Product propylene oxide is discharged in the epoxidation reaction zone 72 by a line 76 and product tertiary butyl alcohol is discharged in the epoxidation reaction zone 72 by a line 78.

In accordance with an embodiment of the present invention, tertiary butyl alcohol in the product line 42 is charged to a methyl tertiary butyl ether reaction zone 200 which is constructed and operated, for example, in the manner disclosed and described in Kruse et al. U.S. Pat. No. 5,243,091. In accordance with this embodiment, methanol is charged to the methyl tertiary butyl ether reaction zone 200 by a line 202 and product methyl tertiary butyl ether is discharged from the methyl tertiary butyl ether reaction zone 200 by a line 204.

Having thus described our invention, what is claimed is:

1. A plural stage process for the production of tertiary butyl alcohol from isobutane which comprises the steps of:

charging isobutane to an oxidation reactor and non-catalytically reacting the isobutane therein with oxygen under reaction conditions including a temperature of about 90° to about 150° C. and a pressure of about 50 to about 1000 psig in order to provide a primary liquid reaction product comprising tertiary butyl alcohol, tertiary butyl hydroperoxide and minor amounts of oxygen-containing by-products including ditertiary butyl peroxide, methanol, methyl formate, acetone and water, said primary liquid reaction mixture comprising about 15 to about 25 wt. % of tertiary butyl hydroperoxide, about 13 to about 20 wt. % of tertiary butyl alcohol, about 50 to about 65 wt. % of unreacted isobutane and about 2 to about 5 wt. % of oxygen-containing impurities, distilling the primary liquid reaction product in a first distillation zone so as to provide a first lighter isobutane recycle distillation fraction and a first heavier liquid distillation fraction comprising the remainder of the primary liquid reaction mixture, diluting the first heavier liquid distillation fraction with an amount of recycle diluent tertiary butyl alcohol sufficient to provide a feed mixture comprising about 15 to 25 wt. % of tertiary butyl hydroperoxide, about 75 to 85 wt. % of tertiary butyl alcohol and minor amounts of oxygen-containing impurities, charging the feed mixture to a hydroperoxide decomposition reactor and contacting it therein with a pelleted solid heterogeneous peroxide decomposition catalyst under hydroperoxide decomposition conditions including a temperature within the range of about 25° to about 250° C., a space velocity of about 0.5 to 5 volumes of tertiary butyl hydroperoxide charge stock per volume of catalyst per hour and a pressure of about 20 to about 1,000 psig to convert substantially all of the tertiary butyl hydroperoxide to a final reaction mixture comprising tertiary butyl alcohol and a minor amount of oxygen-containing by-products, distilling the final reaction mixture in a second distillation zone so as to provide a lighter overhead distillation fraction comprising oxygen and vaporized normally liquid components, and a heavier distillation fraction comprising tertiary butyl alcohol and residual quantities of peroxide contaminants, distilling said heavier distillation fraction in a third distillation zone to provide an overhead tertiary butyl alcohol distillation fraction comprising purified tertiary butyl alcohol and a bottoms distillation fraction comprising heavier reaction by-products and contaminants, recycling a portion of said overhead tertiary butyl alcohol distillation fraction to said first heavier liquid distillation fraction as said recycle diluent tertiary butyl alcohol, recycling a portion of said bottoms distillation fraction to said hydroperoxide decomposition reactor, and recovering the remaining portion of said overhead tertiary butyl alcohol distillation fraction.

* * * * *